United States Patent [19]

Hao

[11] Patent Number: 4,791,191
[45] Date of Patent: Dec. 13, 1988

[54] DEPYROGENATION OF CLINICAL ALBUMIN

[75] Inventor: Yu-Lee Hao, Potomac, Md.

[73] Assignee: Plasmatech Corporation, Potomac, Md.

[21] Appl. No.: 126,120

[22] Filed: Nov. 12, 1987

[51] Int. Cl.$^4$ .............................................. C07K 3/28
[52] U.S. Cl. ................................... 530/364; 424/101; 530/362; 530/380
[58] Field of Search ....................... 530/364, 380, 362; 424/101

[56] References Cited

U.S. PATENT DOCUMENTS

| | | | |
|---|---|---|---|
| 3,992,367 | 11/1976 | Plan et al. | 530/364 |
| 4,156,681 | 5/1979 | Schneider et al. | 530/364 |
| 4,222,934 | 9/1980 | Hao | 530/364 |
| 4,677,194 | 6/1987 | Hao | 530/380 |

OTHER PUBLICATIONS

Skarnes et al., J. Exp. Med. 108, 685–700 (1958).
Wye et al., Vox Sang 32, 182–184 (1977).
Yoshika et al., J. Immunol. 89, 326–335 (1962).
Hao, Vox Sang. 49, 1–8 (1985).
Hao, Vox. Sang. 36: 313–320 (1979).
Cohn et al., JACS, 68, 459–475 (1946).
J. Exp. Med. 110, 731–750 (1959), Landy et al.
Pearson et al., Bio Science 30, 461–464 (1980).
Rall et al., Am. J. Physiol. 188, 559–562 (1957).
Rudbach et al., Nature, 202, 811–812 (1964).
Schneider et al., Blot 30: 121–134 (1975).
Skarnes, Ann. N.Y. Acad. Sci. 133: 644–662 (1966).

Primary Examiner—Howard E. Schain

[57] ABSTRACT

A simple method for the depyrogenation of clinical albumin is disclosed. It includes mixing the pyrogenic clinical albumin with human plasma, followed by a two-step albumin method reported previously by this inventor. The depyrogenated albumin, in the form of ethanol precipitate, can then be processed into clinical albumin according to the conventional procedures. This simple process not only results in the depyrogenation of the endotoxin—contaminated albumin, but also recovers the albumin which is present in the added plasma. The overall albumin yield is greater than 90% as calculated from the starting pyrogenic albumin and the albumin present in the added plasma.

12 Claims, No Drawings

DEPYROGENATION OF CLINICAL ALBUMIN

BACKGROUND AND SUMMARY OF THE INVENTION

The present invention relates to the depyrogenation of endotoxin-contaminated albumin intended for clinical use. More particularly, the present invention is directed to a method in which a pyrogenic lot of clinical albumin can be made non-pyrogenic again, thus avoiding the monetary loss as well as the loss of precious material.

Pyrogenic albumin is caused by the contamination of endotoxins derived from Gram-negative bacteria during the manufacturing process. Because of the ubiquitous nature of bacteria, the control of these physiologically active agents is of utmost importance to the plasma fractionation industry, as well as to the entire pharmaceutical industry. The most positive method of control, strict aseptic techniques that limit microbial contamination, cannot, in most cases, maintain complete sterility throughout the manufacturing process. Therefore, manufacturers may at times find their final product pyrogenic at the bulk solution stage or after the product has been filled in bottles. The result is the loss of the entire lot of precious material.

In the plasma fractionation industry the monetary loss due to pyrogenic albumin must have been in the millions of dollars per year. However, no plasma fractionator has reported any reliable method to depyrogenate its albumin, except that, in casual conversation, they admitted using charcoal, heat-treatment, or depth filtration, all of which are of "hit or miss" in nature. The only published method for depyrogenation of clinical albumin was reported by Wye and Kim (Vox Sang 32: 182–184, 1977) who mixed pyrogenic albumin with Cohn ethanol Fractions IV-1 and IV-4, based on the findings of Yoshika and Johnson (J. Immunol. 89: 326–335, 1962), who found the endotoxin-inactivating activities in these two fractions followed by differential thermal heating to recover albumin according to the method of Schneider et al. (Blut 30: 121–134, 1975) This reported method not only requires an excessive amount of Cohn Fractions IV-1 and IV-4, but also suffers considerable losses of albumin. The yield based on 21 batches was about 75%. In some cases, the procedure was not able to remove the endotoxins from the pyrogenic albumin solutions, thus resulting in the loss of the entire lot. Moreover, the method using differential thermal heating to recover albumin (Schneider et al, 1975) has not been accepted by the U.S. Food and Drug Administration as a licensed procedure for manufacturing clinical albumin.

It has been known since 1954 (Hegemann, Z. Immunitactsforsch 111: 213–225) that normal human plasma or serum has the ability to diminish the pyrogenicity of endotoxins. This observation was confirmed in subsequent years by many reports (Skarnes et al. J. Exp. Med. 108: 685–700, 1958; Rall et al. Am. J. Physiol. 188: 559–562, 1957; Rudbach and Johnson, Nature 202: 811–812, 1964; Yoshika and Johnson, J. Immunol. 89: 326–335, 1962; Landy et al. J. Exp. Med. 110: 731–750, 1959; Skarnes, Ann. N.Y. Acad. Sci. 133: 644–662, 1966). Yoshika and Johnson (1962) fractionated serum by the Cohn ethanol procedure (Cohn et al. JACS 68: 459–475, 1946) and found that Cohn Fraction IV-1 contains the substance(s) which decreases pyrogenicity caused by endotoxins. These finding were further confirmed by this inventor who isolated from human plasma the protein that is responsible for inactivating such bacterial endotoxins (Hao, Y. L. U.S. Pat. No. 4,677,194, 1987).

The present invention would therefore provide a systematic approach to remove endotoxins from pyrogenic albumin renderig it suitable for clinical use again. The method consists of: (1) titration of a given amount of pyrogenic albumin with increasing amounts of plasma until the mixture gives an endotoxin level equal to or less than 0.5 E.U. (endotoxin units)/ml as assayed by the Limulus Amebocyte Lysate (LAL) tests (Pearson and Weary, Bio Science 30: 461–464, 1980); the minimal amount of plasma required to reach such a low level of endotoxin is the amount of plasma to be added to the pyrogenic albumin for its depyrogenation; (2) mixing the required plasma with pyrogenic albumin in a jacketed tank with cooling, and addition of sufficient saline solution, 0.15M NaCl, to the mixture so that the final protein concentration reaches 1.0–2.0%; (3) adjustment of the pH of the mixture to 5.75±0.05 with 0.8M acetate buffer, pH 4.0, according to a previously reported method of this inventor (Hao, Vox Sang 36: 313–320 1979) and cooling the mixture down to 0° to 1° C.; (4) addition of 95% ethanol to the mixture under stirring until a final ethanol concentration reaches 40–42% (v/v). During the addition of ethanol, the temperature of the mixture should not exceed 0° C. After the required amount of ethanol is added, the mixture should be cooled down to −5° to −6° C. under continuous stirring. The protein concentration of this mixture should be in the range of 0.60–1.2% and the sodium content should be 80–90 milliequivalents, or 0.08 to 0.09M NaCl; (5) stirring the mixture for at least 3 hours at −5° to −6° C., the liquid-solid separation is achieved by centrifugation (Sharples centrifuges AS-16 or AS-26) or by filtration (Hao, Vox sang. 49; 1–8, 1985) at a flow rate of approximately 500 ml/min. The supernatant thus obtained is then filtered through depth filter pads, e.g. Cuno 60S at −5° to 6° C.; (6) precipitation of albumin is carried out by adjusting the pH to 4.8±0.05 with acetate buffer (Hao, 1979). After stirring for at least 3 hours, the liquid-solid separation is again achieved by centrifugation at a flow rate of approximately 500 ml/min or by filtration. The paste (Fraction V) thus obtained can then be considered as the regular Fraction V and processed into non-pyrogenic clinical albumin according to the conventional procedures (Cohn et al., 1946 and Hao, 1979).

DESCRIPTION OF THE PREFERRED EMBODIMENTS

In the method of the present invention for depyrogenation of albumin on a large scale, the method was carried out in a series of steps which are described hereinafter as Example 1.

The pyrogenic albumin solution or plasma protein fraction (PPF) can be 4%, 5%, 20%, 25% or any other concentration. If albumin powder is used, it can be dissolved in pyrogen-free water containing 0.15M NaCl to a final concentration of 1 to 2% protein. The blood plasma (or serum) used for depyrogenation can be fresh frozen plasma, cryo supernatant from fresh frozen plasma, or outdated plasma.

Example 1

(I) Titration of Pyrogenic Albumin with Increasing Amounts of Plasma

One ml of pyrogenic albumin is mixed with 0.1, 0.2, 0.3 ml . . . of plasma in test tubes and the mixtures, after thorough mixing, are placed in a dry or water bath for 30 min. at 37° C. An aliquot, 0.1 ml of each tube, is then pipetted into a 10×75 mm test tube to which 0.1 ml of Limulus Amebocyte Lysate (LAL) having a sensitivity of 0.5 E.U./ml is also added. In order to assure that the LAL tests are carried out correctly, a negative control consisting of 0.1 ml each of pyrogen-free water and LAL, and a positive control consisting of 0.1 ml each of endotoxin standard having 0.5 E.U./ml and LAL are also included All tubes are then placed in an incubator block for 60 min. at 37° C. After incubation, each tube is inverted 180°. If the contents in the tube run along the wall, it is considered negative. If the contents in the tube stay in the bottom of the tube as a clot, it is considered positive indicating that at least 0.5 E.U/ml is present in the sample being tested (Pearson and Weary, 1980). Using this titration method, negative control should be negative and positive control should be positive. Otherwise, the titration has to be repeated. The least amount of plasma which gives the negative LAL test is the amount of plasma required to depyrogenate the given lot of pyrogenic albumin. For example, if the mixture of 0.2 ml plasma for every ml of pyrogenic albumin gives a negative LAL test under the above described conditions, the depyrogenation process should be carried out by mixing with 200 ml plasma for every 1,000 ml of pyrogenic albumin.

(II) Process for Depyrogenation of Albumin

The process is presented in the form of a flow chart. It should be noted that in actual manufacturing process, weight in kg. rather than volume is used.

Flow Chart for Depyrogenation of 1,000 kg
of a 5% Albumin Solution Which
Requires 200 kg Plasma Pyrogenic Albumin, 5% solution + Plasma, (approx. 6% protein)
(1000 kg)                         (200 kg)

Total protein = 1000 × 5 × 10     Total protein = 200 × 6 × 10
             = 50,000 g                        = 12,000 g (1) The amount of 0.15 M NaCl solution
to be added = $\frac{50,000 + 12,000}{2 \times 10}$ −
1,200 kg = 1,900 kg
in order to reach a final protein
concentration of 2%.
(2) Acetate buffer added to reach pH
5.75 ± 0.05 is approx. 5 kg.
(3) The amount of 95% ethanol needed =
$(1,200 + 1,900 + 5) \times \frac{42}{95 - 42} \times$
0.82 (specific gravity of
95% ethanol) = 2,018 kg

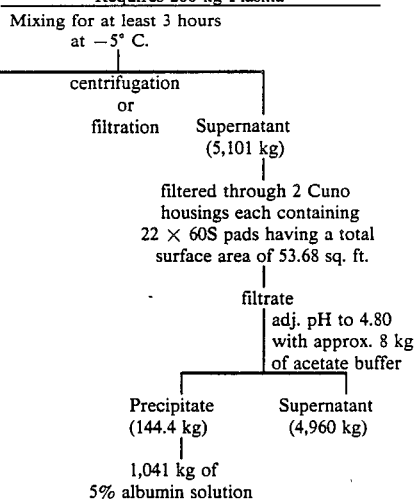

-continued
Flow Chart for Depyrogenation of 1,000 kg
of a 5% Albumin Solution Which
Requires 200 kg Plasma Yield calculation:

The density of 5% albumin solution is 1.009 g/ml, whereas the density of plasma is 1.025 g/ml. It is generally assumed that every liter of plasma contains approximately 32 g albumin. The total amount of pyrogenic albumin, in grams, in the starting mixture is therefore $$\frac{1,000 \text{ kg}}{1.009 \text{ kg/L}} \times 5 \text{ g} \times 10 + \frac{200 \text{ kg}}{1.025 \text{ kg/L}} \times 32 \text{ g} \times 10 = 55,798 \text{ g}.$$

The total amount of albumin, in grams, in 1,041 kg of pyrogen-free 5% albumin solution is $$\frac{1,041 \text{ kg}}{1.009 \text{ kg/L}} \times 5 \text{ g} \times 10 = 51,585 \text{ g}.$$

The overall yield of this depyrogenation process is therefore equal to $$\frac{51,585}{55,798} \times 100 = 92.5\%.$$

It is thought that the invention and many of its attendant advantages will be understood from the foregoing description, and it will be apparent that various changes may be made in the method as described herein without departing from the spirit and scope of the invention or sacrificing its material advantages, the forms hereinbefore described being merely preferred embodiments thereof.

The embodiments of the invention in which an exclusive property or privilege is claimed are defined as follows:

1. A method for the depyrogenation of clinical albumin comprising:
   (a) mixing at least the titrated amount of plasma with a given amount of pyrogenic albumin rendering the mixture non-pyrogenic as assayed by LAL test:
   (b) addition of physiological saline, 0.15 NaCl, to the mixture so that the protein concentration of 1.0 to 2.0% is reached;
   (c) adjusting the pH of the mixture to 5.75±0.05;
   (d) precipitation of endotoxins and impurities in the reaction mixture by the addition of ethanol in an amount sufficient to give a final concentration of 42% at pH of 5.85±0.05 at temperature of −5° to −6° C.;

(e) removal of endotoxins and impurities as precipitate by centrifugation followed by filtration, or by direct filtration;

(f) precipitating albumin from the said filtrate at pH 4.8 and recovery of albumin paste by centrifugation or filtration.

2. The method of claim 1 in which the plasma to be added is fresh frozen plasma, cryo supernatant from fresh frozen plasma or outdated plasma.

3. The method of claim 1 in which the pyrogenic albumin solution is 4%, 5%, 20%, or 25%.

4. The method of claim 1 in which the pyrogenic albumin is in lyophilized powder form.

5. The method of claim 1 in which the pyrogenic solution is 5% plasma protein fraction (PPF).

6. The method of claim 1 in which the dilution of the mixture of pyrogenic albumin and plasma is achieved by the addition of sodium chloride solution of the concentration of 0.05–0.25M.

7. The method of claim 1 in which the saline diluted mixture is adjusted to a pH range of 5.5 to 6.0.

8. The method in claim 1 in which the endotoxins and impurities are removed at an ethanol concentration of 36–48% at a pH range of 5.6 to 6.2.

9. The method in claim 1 in which the endotoxins and impurities are removed by centrifugation followed by filtration.

10. The method of claim 1 in which the endotoxins and impurities are removed by filtration.

11. The method in claim 1 in which the albumin is recovered from the said filtrate in claims 9 or 10 by precipitation at a pH range of 4.4 to 5.2 followed by centrifugation to obtain albumin paste.

12. The method in claim 1 in which the albumin is recovered from the filtrate in claims 9 or 10 by ultrafiltration and diafiltration.

* * * * *